US006844326B2

(12) United States Patent
Li

(10) Patent No.: US 6,844,326 B2
(45) Date of Patent: Jan. 18, 2005

(54) TREATMENT OF ALOPECIA

(75) Inventor: Lingna Li, San Diego, CA (US)

(73) Assignee: AntiCancer, Inc., San Diego, CA (US)

( * ) Notice: Subject to any disclaimer, the term of this patent is extended or adjusted under 35 U.S.C. 154(b) by 45 days.

(21) Appl. No.: 10/199,757

(22) Filed: Jul. 17, 2002

(65) Prior Publication Data
US 2003/0059464 A1 Mar. 27, 2003

Related U.S. Application Data

(60) Continuation of application No. 09/427,699, filed on Oct. 27, 1999, now abandoned, which is a continuation-in-part of application No. 08/859,051, filed on May 20, 1997, now Pat. No. 6,733,776, which is a division of application No. 08/858,469, filed on May 20, 1997, now Pat. No. 5,914,126, which is a division of application No. 08/486,520, filed on Jun. 7, 1995, now Pat. No. 5,753,263.
(60) Provisional application No. 60/105,831, filed on Oct. 27, 1998.

(51) Int. Cl.[7] .................. A01N 43/04; A01N 63/00; A61K 9/127; C12N 15/00; C12N 15/63
(52) U.S. Cl. .................. 514/44; 424/93.21; 424/450; 435/320.1; 435/455
(58) Field of Search .................. 514/44; 435/320.1, 435/455; 424/93.21, 450

(56) References Cited

U.S. PATENT DOCUMENTS

| 4,755,388 A | 7/1988 | Heath et al. ............. 424/450 |
| 4,919,664 A | 4/1990 | Oliver et al. ............. 623/15 |
| 4,925,661 A | 5/1990 | Huang ............. 424/178.1 |
| 4,957,735 A | 9/1990 | Huang ............. 424/178.1 |
| 5,077,211 A | 12/1991 | Yarosh ............. 435/193 |
| 5,130,142 A | 7/1992 | Wong et al. ............. 424/574 |
| 5,190,762 A | 3/1993 | Yarosh ............. 424/450 |
| 5,223,263 A | 6/1993 | Hostetler et al. ............. 424/450 |
| 5,302,389 A | 4/1994 | Kripke et al. ............. 424/94.6 |
| 5,384,126 A | 1/1995 | Bonte et al. ............. 424/450 |
| 5,486,509 A | 1/1996 | Jimenez et al. ............. 514/167 |
| 5,556,956 A | 9/1996 | Roy et al. ............. 536/24.1 |
| 5,618,798 A | 4/1997 | Bar-Shalom et al. ............. 514/53 |
| 5,723,146 A | 3/1998 | Rossling et al. ............. 424/450 |
| 5,723,149 A | 3/1998 | Bonte et al. ............. 424/450 |
| 5,753,263 A | 5/1998 | Lishko et al. ............. 424/450 |

FOREIGN PATENT DOCUMENTS

| DE | 4113346 | 10/1992 |
| EP | 369105 | 5/1990 |
| FR | 2648132 | 12/1990 |
| FR | 2669225 | 5/1992 |
| WO | WO 88/07362 | 10/1988 |
| WO | WO 91/07945 | 6/1991 |
| WO | WO 92/00057 | 1/1992 |

OTHER PUBLICATIONS

Anderson. Human Gene Therapy 392:25–30 (1998).
Gregoriadis, "Liposomes For Drugs And Vaccines," Trends in Biotechnology (1985) 3(9):235–41.
Hoffman et al., "Binding and Entrapment of High Molecular Weight DNA by Lecithin Liposomes," FEBS Letters (1978) 93(2):365–8.
Jimenez et al., "Treatment with ImuVert/N–Acetylcysteine Protects Rats from Cyclophosphamide/Cytarabine–Induced Alopecia," Cancer Invest (1992)10(4):271–276.
Juliano et al., "Liposomes as a Drug Delivery System for Antisens Oligonucleotides," Antisense Research and Development (1992) 2:165–176.
Li et al., "Liposomes can Specifically Target Entrapped Melanin to Hair Follicles in Histocultured Skin," In Vitro Cell Dev Biol (1993) 29A:192–194.
Li et al., "Product–Delivering Liposomes Specifically Target Hair Follicles in Histocultured Intact Skin," In Vitro Cell Dev Biol (1992) 28A:679–81.
Lieb et al., "Topical Delivery Enhancement with Multilamellar Liposomes into Pilosebaceous Units: I. In Vitro Evaluation Using Fluorescent Techniques with the Hamster Ear Model," J Investigative Dermatolgy (1992) 99(1):108–13.
Ludin et al. "Application of Novel Vectors for GRP–Tagging of Proteins to Study Microtubule–Associated Proteins" Elsevier Science pp. 107–111 (1996).
Maigach et al., "Regional Variation in Percutaneous Penetration in Man," Arch Environ Health (1971) 23:208–11.
Mezei et al., "Liposomes—A Selective Drug Delivery System for the Topical Route of Administration," Life Sciences (1980) 26:1473–1477.
Rowe et al., "Treatment of Hirsutism with Liposomal Progesterone," Prostate (1984) 5:346–347.
Plessis et al., "Topical Delivery of Liposomally Encapsulated Gamma–Interferon," Antiviral Res (1992) 18:259–265.
Schmidt, K. H. ed., "Liposomes As Drug Carriers," Stuttgart: George Thieme Verlag (1986).

Primary Examiner—Shin-Lin Chen
(74) Attorney, Agent, or Firm—Morrison & Foerster LLP

(57) ABSTRACT

A composition and method for treating and monitoring alopecia by altering hair follicle cells to produce a cell cycle inhibitor is disclosed.

6 Claims, No Drawings

SEQUENCE LISTING

```
<160> NUMBER OF SEQ ID NOS: 2

<210> SEQ ID NO 1
<211> LENGTH: 26
<212> TYPE: DNA
<213> ORGANISM: Artificial Sequence
<220> FEATURE:
<223> OTHER INFORMATION: Upstream primer

<400> SEQUENCE: 1
ccgctcgaga tgtcagaacc ggctgg                                    26

<210> SEQ ID NO 2
<211> LENGTH: 29
```

-continued

```
<212> TYPE: DNA
<213> ORGANISM: Artificial Sequence
<220> FEATURE:
<223> OTHER INFORMATION: Downstream primer

<400> SEQUENCE: 2
cgcggattct tagggcttcc tcttggact                                  29
```

TREATMENT OF ALOPECIA

This application is a continuation of U.S. Ser. No. 09/427,699, filed 27 Oct. 1999 abandoned which is a continuation-in-part of U.S. Ser. No. 08/859,051, filed 20 May 1997 now U.S. Pat. No. 6,733,776 which is a divisional of U.S. Ser. No. 08/858,469, filed 20 May 1997 and now U.S. Pat. No. 5,914,126 which is a divisional application of U.S. Ser. No. 08/486,520, filed 7 Jun. 1995 and now U.S. Pat. No. 5,753,263. This application also claims priority under 35 U.S.C. § 119 from provisional application 60/105,831 filed 27 Oct. 1998. The contents of these applications are incorporated herein by reference.

TECHNICAL FIELD

This invention relates to methods for specifically delivering cell cycle inhibitors to hair follicles to inhibit alopecia. In particular, the invention relates to specifically delivering the cell-cycle inhibitor, p21 to hair follicles.

BACKGROUND ART

Many chemotherapeutic agents, for example, antimetabolites (methotrexate, 5-fluoouracil, cytarabine), alkylating agents (cyclophosphamide, mechlorethamine, dacarbazine, ifosfamide), antineoplatic antibiotics (bleomycin, actinomycin D, daunomycin, doxorubicin, mitoxantrone), the vinca alkaloids (vincistine, vinblastine) and taxanes (Taxol, Taxotere), produce an anagen effluvium to induce alopecia by killing the active proliferating cells of the hair matrix. Scalp hair is particularly sensitive since 85% of scalp hair is in anagen phase. Chemotherapy-induced alopecia (CIA) is thus a major problem in clinical oncology, which can be a major obstacle for patients to accept chemotherapy. It is particularly devastating to women as alopecia-inducing agents such as the taxanes are becoming more frequently used in breast and ovarian cancers.

Surgical transplantation of small, discrete, skin areas having viable follicles to areas having inactive follicles is expensive, labor-intensive and relatively short-lasting. Also, as described by R. F. Oliver et al. in U.S. Pat. No. 4,919,664, follicular dermal cells can be inserted into a skin incision, resulting in hair growth along the incision. However, this is a complex technique that does nothing to stimulate existing follicles. Treatment of the hair and skin with various creams or lotions with biologically active ingredients to improve hair growth has generally low efficiency. Attempts to follow this approach have been ineffective, possibly because of the inability of stimulators to penetrate the cellular membrane of hair follicle cells and to enter into the cells where their action is needed.

Liposomes, which are artificial phospholipid vesicles, have been successfully used for delivery of different low-molecular-weight water-soluble and oil-soluble compounds into different cells. See, for example, G. Gregoriadis, *Trends in Biotechnology* (1985) 3:235–241 and K. H. Schmidt, ed., *Liposomes as Drug Carriers*, Stuttgart:George Thieme Verlag (1986). The applications and issued patents from which priority is claimed describe the use of liposomes to target hair follicles specifically.

No pharmacological agent inhibits CIA in a reliable, cost-efficient, unharmful and long-lasting manner. The treatment of human hair loss, especially CIA is important and beneficial for cancer patients and other persons generally. Thus, new agents and treatments for the prevention of CIA are needed.

It has been verified, as exemplified below, that chemotherapy-induced alopecia can be almost completely prevented in skin histoculture by liposome targeting of the gene encoding the cyclin-dependent-kinase inhibitor p21 to the hair follicle.

SUMMARY OF THE INVENTION

Generally, the present invention is directed to methods to inhibit chemotherapy-induced alopecia by selective delivery of expression systems for cell cycle inhibitors to the hair follicles.

In another aspect, the invention is directed to a method to monitor the expression of p21 in cells which method comprises assessing the fluorescence of the cells that have been treated with an expression system for a fusion protein, which comprises an amino acid sequence conferring p21 activity linked to an amino acid sequence which effects emission of fluorescent light. The fluorescence may be observed in vitro or in vivo, even in the live subject.

DETAILED DESCRIPTION OF THE INVENTION

Cyclin-dependent kinase inhibitor (CDIs) proteins are important because they regulate CDKs at specific points in the cell cycle and can therefore negatively control progression of the cell cycle. See Hirama et al. *Blood* (1995) 86:841–854; Polyak et al. *Gene Dev* (1994) 8:9; Toyoshima et al. *Cell* (1994) 78:67; Serrano et al. *Nature* (1993) 366:704; Serrano et al. *Science* (1995) 267:249. The mammalian CDIs include p21, p20, p27, p28, p16, p15 and p18. The p21 protein is a potent inhibitor of all cyclin/CDK complexes tested, including cyclin/CDK2 and cyclin D/CDK4. The p21 protein can inhibit DNA replication in the absence of cyclin/CDK by binding to PCNA and inhibiting its ability to activate DNA polymerase $\delta$ and thus p21 can stop DNA synthesis and inhibit cells from entering S-phase. Waga et al. *Nature* (1994) 369:574. Therapeutic application of p21 puts the hair-follicle into a resting state (telogen) to protect against toxic events such as chemotherapy-induced alopecia (CIA).

The hair follicle is a complex mini-organ driven by a biological clock in a rhythmic, cyclic fashion from stages of resting (telogen) to growth (anagen) and via a short regression phase (catagen) back to the telogen phase. See Chase, H. B. *Physiol Rev* (1954) 34:113–26; Orfanos, C. E., Happle, R. (eds.) *Hair Growth and Hair Diseases,* Springer, Berlin (1990); Rook, A., Dawber, R. (eds.) *Diseases of the Hair and Scalp,* Blackwell, Oxford (1992). Cytotoxic agents damage cycling hair matrix cells to cause "anagen effluvium" and eventually induce alopecia. See Hood et al. *Cancer Medicine,* 4th ed. Williams & Wilkins. 1:3141 (1997).

An in vitro model for studying the anagen phase of the murine hair cycle for almost the entire duration has been developed. In this model, catagen can be induced by chemotherapeutic drugs. This in vitro system is based on the collagen-sponge-gel-matrix supported histoculture technology adapted for hair-producing skin culture. See Li et al. *Proc Natl Acad Sci USA* (1992) 88:1908–12; Li et al. *In vitro Cell Dev Biol* (1992) 28A:479–481, 695–698, 679–681; Li et al. *In vitro Cell Dev Biol* (1993) 29A:192–194, 258–260, 449–450; Li et al. *In vitro Cell Dev Biol* (1994) 30A:135–138. The skin histoculture technology provides an opportunity to observe, characterize, analyze and manipulate the development of anagen (growth) and catagen (breakdown) in mature hair follicles in vitro in full-thickness skin. The skin histoculture system may also be used to induce CIA with actual hair loss observed in vitro.

Recently, two animal models have been used for studying CIA. It has been demonstrated that the new-born rat is a model for CIA with doxorubicin and cyclophosphamide/cytosine arabinoside. See Jimenez et al. *Cancer Invest* (1992) 10:271–276. The doxorubicin-induced alopecia in new-born rats was prevented by 1,25-dihydroxyvitamin $D_3$ and the cyclophosphamide-induced alopecia was prevented by ImuVert/N-acetylcysteine. Also reported is a murine model for inducing and manipulating hair follicle regression (catagen) and CIA. See Paus et al. *J Invest Derm* (1994) 103:143–147; Paus et al. *Cancer Research* (1996) 56:4438–4443; Paus et al. *Am J Pathol* (1994) 144:719–734. The massive catagen development in anagen C57B1–6 mice can be achieved after topical treatment with dexamethasone once daily. CIA evidenced by dystrophic anagen, catagen and disruption of melanization of hair follicles was established in C57B1–6 mice with a single intraperitoneal injection of cyclophosphamide. See Hoffman, R. M. *J Cell Pharmacol* (1991) 2:189–201. Topical application of immunophilin ligands such as cyclosporin A and FK506 can induce active hair growth in telogen C57B16 mice and also inhibit massive, dexamethasone-induced, premature catagen development. See Maurer et al. *Am J Pathol* (1997) 150:1433–1441.

This invention provides uniquely effective protocols and materials for the treatment of CIA, as well as assay systems for monitoring hair follicle cells and hair growth. The cyclin-dependent kinase (CDK) inhibitors including p21, p16 and p27 may be used to put the hair follicle into a resting, chemo-resistant phase to prevent CIA.

The expression systems employed in the present invention generally comprise a nucleotide sequence encoding a cell-cycle inhibitor such as the p21 protein operably linked to sequences which effect expression of the coding sequence. Vectors for delivery of the nucleotide sequence encoding a cell-cycle inhibitor may also effect the insertion of the nucleotide sequence into the genome of the host, thus employing the endogenous control sequences to effect expression.

If the vector contains an expression system, suitable promoters and enhancers can be used. General constitutive promoters such as SV40 or CMV promoters can be included, along with their enhancer elements, or tissue-specific promoters may be used to enhance specificity. Means to construct suitable vectors for delivery of a gene along with provision for its expression are well known in the art.

In order to effect the modification of cells for the expression of the cell-cycle inhibitor, the expression system or integrating encoding nucleotide sequence must be formulated so as to enter the cell. Integration of the desired nucleotide sequences into viral vectors, such as adenovirus may provide this means of entry. However, retroviral vectors, or other mediators of cellular uptake, such as lipids, or various liposomal type formulations or emulsions are preferred.

It is also part of the invention to employ the protein exhibiting cell-cycle inhibition as a fusion protein to a reporter amino acid sequence, most preferably an amino acid sequence which confers fluorescence on the fusion protein. The use of green fluorescent protein (GFP) to confer fluorescence on a fusion protein is well understood in the art; see, for example, Chalfie, M., et al. *Science* (1994) 263:802–805. The expression system may be targeted to the hair follicle cells of interest by utilizing liposome-mediated delivery as described in U.S. Pat. No. 5,641,508, filed Jan. 13, 1994, and incorporated herein by reference.

The invention contemplates using the expression system to study and treat chemotherapy-induced alopecia (CIA). Similarly, the invention contemplates using the expression system in in vitro and animal models to determine the effects of various substances on CIA.

A therapeutic composition contains the expression system of the present invention. A therapeutically effective amount of the expression system and, if present, other beneficial compounds, is a predetermined amount calculated to achieve the desired effects, i.e., to effectively affect the pigmentation of the skin or hair cells. Thus, an effective amount can be measured by improvements in one or more symptoms associated skin or hair cell growth in the subject.

The dosage can be adjusted by the individual physician in the event of any complication. The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the conditions of administration. Suitable regimes for administration are also variable, but are typified by an initial administration followed by repeated doses at one or more hour intervals by a subsequent administration.

The choice of vector to which a DNA segment of the present invention is operatively linked depends directly, as is well known in the art, on the functional properties desired, e.g., protein expression, and the host cell to be transformed, these being limitations inherent in the art of constructing recombinant DNA molecules. However, a vector contemplated by the present invention is at least capable of directing the replication, and preferably also expression, of the beneficial protein structural gene included in DNA segments to which it is operatively linked.

In preferred embodiments, a vector contemplated by the present invention includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon also include a gene whose expression confers drug resistance to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of the beneficial protein gene in a bacterial host cell, such as *E. coli*, transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmid are pUC8, pUC9, pBR322 and pBR329 available from Biorad Laboratories, (Richmond, Calif.) and pPL and pKK223 available from Pharmacia, Piscataway, N.J.

Expression vectors compatible with eucaryotic cells, preferably those compatible with mammalian cells, and particularly hair follicle cells, can also be used to form the recombinant DNA molecules for use in the present invention. Mammalian cell expression vectors are well known in the art and are available from several commercial sources. Typically, such vectors are provided containing convenient restriction sites for insertion of the desired DNA segment, and provide the signals required for gene expression in a mammalian cell. Typical of such vectors are the pREP series vectors and pEBVhis available from Invitrogen (San Diego, Calif.), the vectors pTDT1 (ATCC #31255), pCP1 (ATCC #37351) and pJ4W (ATCC #37720) available from the American Type Culture Collection (ATCC) and the like mammalian expression vectors.

Particularly preferred are mammalian expression vectors which allow the expression of the gene in a tissue-specific manner, in this case by the action of a regulatory promotor that will limit gene expression to hair follicle cells.

Successful transformation of the target tissue can be confirmed by evaluation of the target tissue for indicia of function exerted by the administered beneficial compound. For example, where the compound is a nucleic acid expressing p21 protein, as described in the Examples, successful transformation can be detected by evaluating the cell cycle phases of the cells in the target tissue.

The following examples are intended to illustrate but not to limit the invention.

EXAMPLE 1

Cloning of Human p21 Gene

The nucleotide sequence encoding the human p21 gene was amplified by PCR from plasmid MBP-p21, Zhang et al. *Gene* (1994) 3:1750–1758 (1994). Oligomers were designed according to the sequence of the human p21 gene. Xiong et al. *Nature* (1993) 366:701. The upstream primer was

5'-CCG CTC GAG ATG TCA GAA CCG GCT GG-3' (SEQ ID NO:1).

The downstream primer was

5'-CGC GGA TTC TTA GGG CTT CCT CTT GGA CT-3'(SEQ ID NO:2).

The PCR primer reaction conditions were as follows: first denaturation at 94° C. for 10 mm; then 30 cycles of denaturation at 94° C. for 30 s; annealing at 50° C. for 30 s; and extension at 72° C. for 45 s; then a final extension at 72° C. for 10 min.

Electrophoretic analysis demonstrated that the amplified products had the predicted size of 500 bp.

EXAMPLE 2

Construction of pEGFP-p21

The vector pEGFP-$C_3$ (Clonetech, Palo Alto, Calif.), encodes a red-shifted variant of wild-type GFP that has been optimized for brighter fluorescence and higher expression in mammalian cells. The multiple cloning site (MCS) in pEGFP-$C_3$ is between the EGFP coding sequences and the SV40 polyA. Genes cloned into the MCS will be expressed as fusion to the C-terminus of EGFP if they are in the same reading frame (Neo$^R$) contained in the vector allows stable transfected eukaryotic cells to be selected using G418.

The 500 bp p21 amplified gene was cloned into the XhoI/BamHI cloning site of the pEGFP-$C_3$ vector to obtain pEGFP-p21, and correct insertion confirmed by restriction enzyme analysis.

EXAMPLE 3

Histoculture of Skin and Transfection of Cultured Skin with pEGFP-p21 Vector Baby balb-c mice (2 weeks) were treated with hair remover. Small pieces of mouse skin (2×5×2 mm) were cut with a scissors and put onto collagen-containing gels in histoculture in Eagle's minimum essential medium (MEM) supplemented with 10% fetal bovine serum and gentamycin, as described by Li et al. PNAS USA (1991) 88:1908–1912. Cultures were maintained at 37° C. in a gassed incubator with 5% $CO_2$. Liposome interaction with the skin was initiated after 24 hours of histoculture.

40 ml of LipoTAXI transfection reagent (Stratagene, San Diego, Calif.) were added to 20 ml (10 μg) of pEGFP-p21 plasmid DNA, then mixed and incubated for 30 min. at room temperature. 400 μl of serum-free MEM was added to the mixture, then transferred to the skin-culture dish with swirling and the mixtures were incubated for 4 hours at 37° C. The medium was replaced with 2 ml of MEM with 10% serum and incubated for 48 hours at 37° in 5% $CO_2$.

A Nikon fluorescence microscope, equipped with aGFP cubes was used to observe expression. The EGFP-p21 gene was expressed selectively in hair follicles as visualized by bright GFP fluorescence.

Incorporation by Reference

All publications, patents, and patent applications cited herein are expressly incorporated by reference.

What is claimed is:

1. A method to inhibit chemotherapy-induced alopecia which method comprises delivering p21 protein to hair follicles of a mammal, said delivering comprising the step of applying topically to skin areas of a mammal having a plurality of hair follicles, an effective amount of a nucleotide sequence encoding a nucleotide sequence encoding a cyclin-dependent kinase inhibitor p21 protein which upon expression provides p21 protein to the hair follicle cells of said mammal.

2. The method of claim 1 wherein said nucleotide sequence is operably linked to control sequences to effect its expression.

3. The method of claim 1 wherein said nucleotide sequence is contained in a vector.

4. The method of claim 3 wherein said vector is a viral vector.

5. The method of claim 3 wherein said vector is contained in a liposomal formulation.

6. The method of claim 1 wherein said nucleotide sequence encoding p21 protein is contained in a liposomal formulation.

* * * * *